(12) United States Patent
Heuer

(10) Patent No.: US 11,419,643 B2
(45) Date of Patent: Aug. 23, 2022

(54) DEVICE FOR CORRECTING BONE FRACTURES

(71) Applicant: SILONY MEDICAL INTERNATIONAL AG, Frauenfeld (CH)

(72) Inventor: Frank Heuer, Filderstadt (DE)

(73) Assignee: SILONY MEDICAL INTERNATIONAL AG, Frauenfeld (CH)

( * ) Notice: Subject to any disclaimer, the term of this patent is extended or adjusted under 35 U.S.C. 154(b) by 0 days.

(21) Appl. No.: 17/257,335

(22) PCT Filed: Jul. 4, 2019

(86) PCT No.: PCT/EP2019/067967
§ 371 (c)(1),
(2) Date: Dec. 31, 2020

(87) PCT Pub. No.: WO2020/007968
PCT Pub. Date: Jan. 9, 2020

(65) Prior Publication Data
US 2021/0275234 A1    Sep. 9, 2021

(30) Foreign Application Priority Data

Jul. 4, 2018 (DE) .................... 10 2018 116 177.8

(51) Int. Cl.
*A61B 17/70* (2006.01)
(52) U.S. Cl.
CPC ...... *A61B 17/7085* (2013.01); *A61B 17/7014* (2013.01); *A61B 17/7077* (2013.01); *A61B 17/7082* (2013.01)

(58) Field of Classification Search
CPC ...................................... A61B 17/7074–7092
See application file for complete search history.

(56) References Cited

U.S. PATENT DOCUMENTS

| 1,920,821 | A | * | 8/1933 | Wassenaar | A61B 17/6408 |
|---|---|---|---|---|---|
| | | | | | 606/86 R |
| 6,063,090 | A | | 5/2000 | Schlapfer | |
| 9,480,504 | B1 | * | 11/2016 | Schafer | A61B 17/7083 |
| 9,907,582 | B1 | * | 3/2018 | Olea | A61B 17/60 |
| 2005/0234449 | A1 | * | 10/2005 | Aferzon | A61B 17/7089 |
| | | | | | 606/86 A |
| 2005/0245928 | A1 | * | 11/2005 | Colleran | A61B 17/708 |
| | | | | | 606/90 |

(Continued)

FOREIGN PATENT DOCUMENTS

DE    102016121054 B3    4/2018

OTHER PUBLICATIONS

International Search Report Form PCT/ISA/210, and Written Opinion Form PCT/ISA/237, International Application No. PCT/EP2019/067967 pp. 1-10 International Filing Date Jul. 4, 2019 dated Oct. 4, 2019.

(Continued)

*Primary Examiner* — Eduardo C Robert
*Assistant Examiner* — Steven J Cotroneo
(74) *Attorney, Agent, or Firm* — George McGuire

(57) ABSTRACT

The invention relates to a device for correcting a bone fracture using bone anchors, in particular bone screws, and extension devices attachable to the bone anchors.

13 Claims, 14 Drawing Sheets

(56) References Cited

U.S. PATENT DOCUMENTS

| | | | | |
|---|---|---|---|---|
| 2008/0077155 A1* | 3/2008 | Diederich | ............ | A61B 17/708 606/105 |
| 2009/0076515 A1* | 3/2009 | Lamartina | ............ | A61B 17/025 606/90 |
| 2010/0274252 A1* | 10/2010 | Bottomley | ........... | A61B 17/708 606/90 |
| 2011/0077689 A1* | 3/2011 | Mickiewicz | ......... | A61B 17/708 606/277 |
| 2012/0191143 A1* | 7/2012 | Nayet | .................. | A61B 17/708 606/86 A |
| 2014/0277151 A1* | 9/2014 | Fowler | ............... | A61B 17/7074 606/265 |
| 2015/0066088 A1* | 3/2015 | Brinkman | .......... | A61B 17/7077 606/264 |
| 2015/0313585 A1* | 11/2015 | Abidin | ............... | A61B 17/0206 600/213 |
| 2015/0320458 A1* | 11/2015 | Rezach | ............. | A61B 17/7085 606/279 |
| 2017/0311985 A1* | 11/2017 | Bobbitt | ............. | A61B 17/7001 |
| 2018/0214189 A1* | 8/2018 | Olea | ................. | A61B 17/7077 |
| 2020/0054361 A1* | 2/2020 | Peultier | ............. | A61B 17/7085 |

OTHER PUBLICATIONS

German Examination Report, pp. 1-7.

* cited by examiner

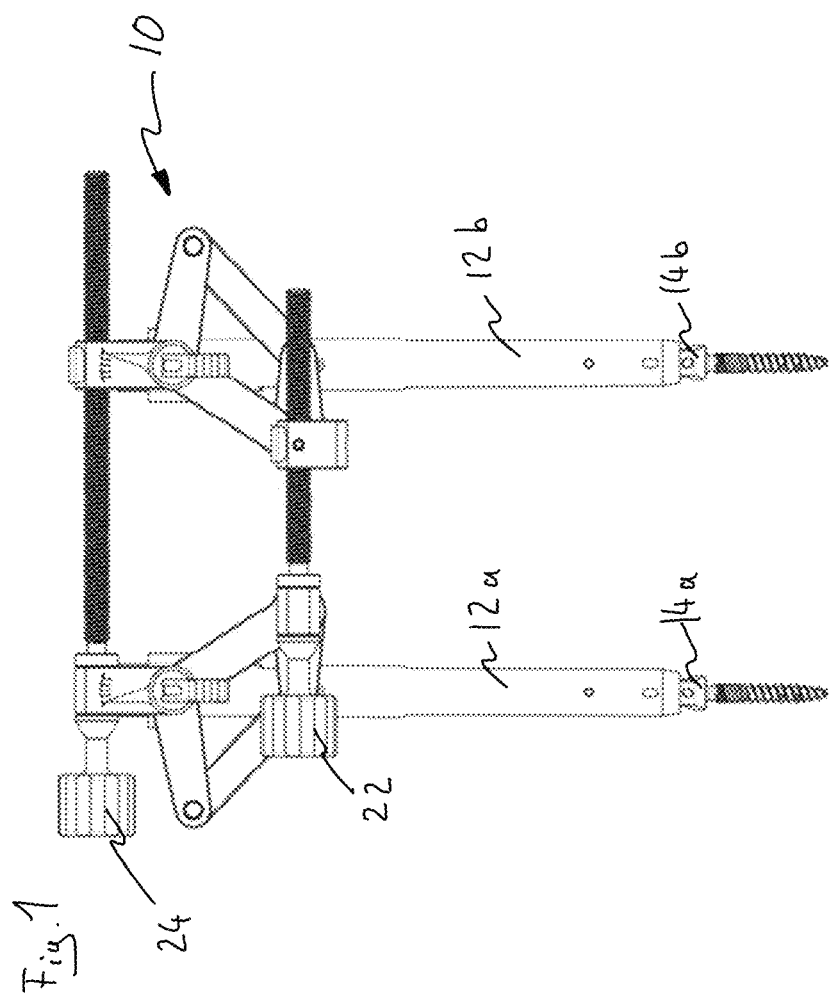

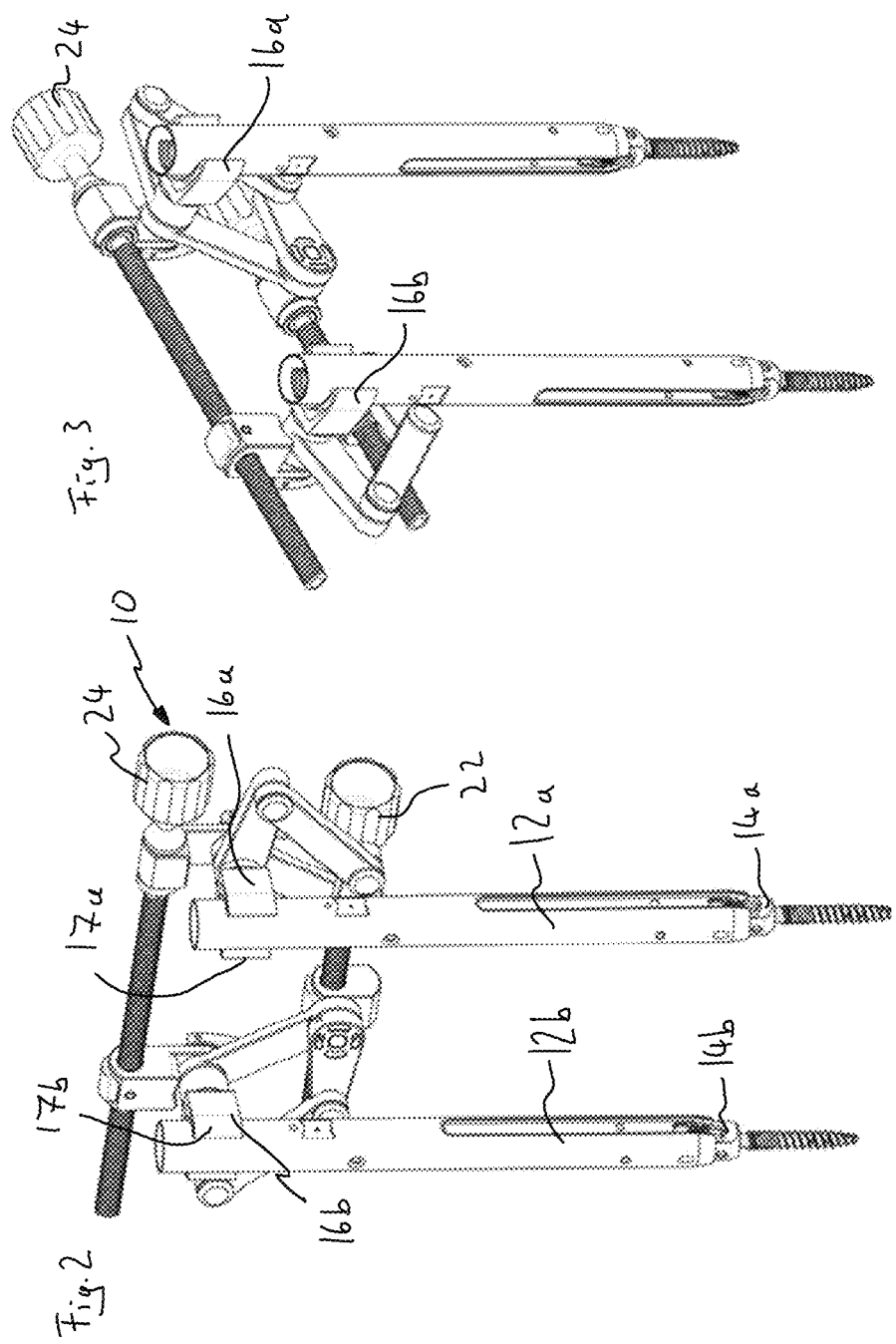

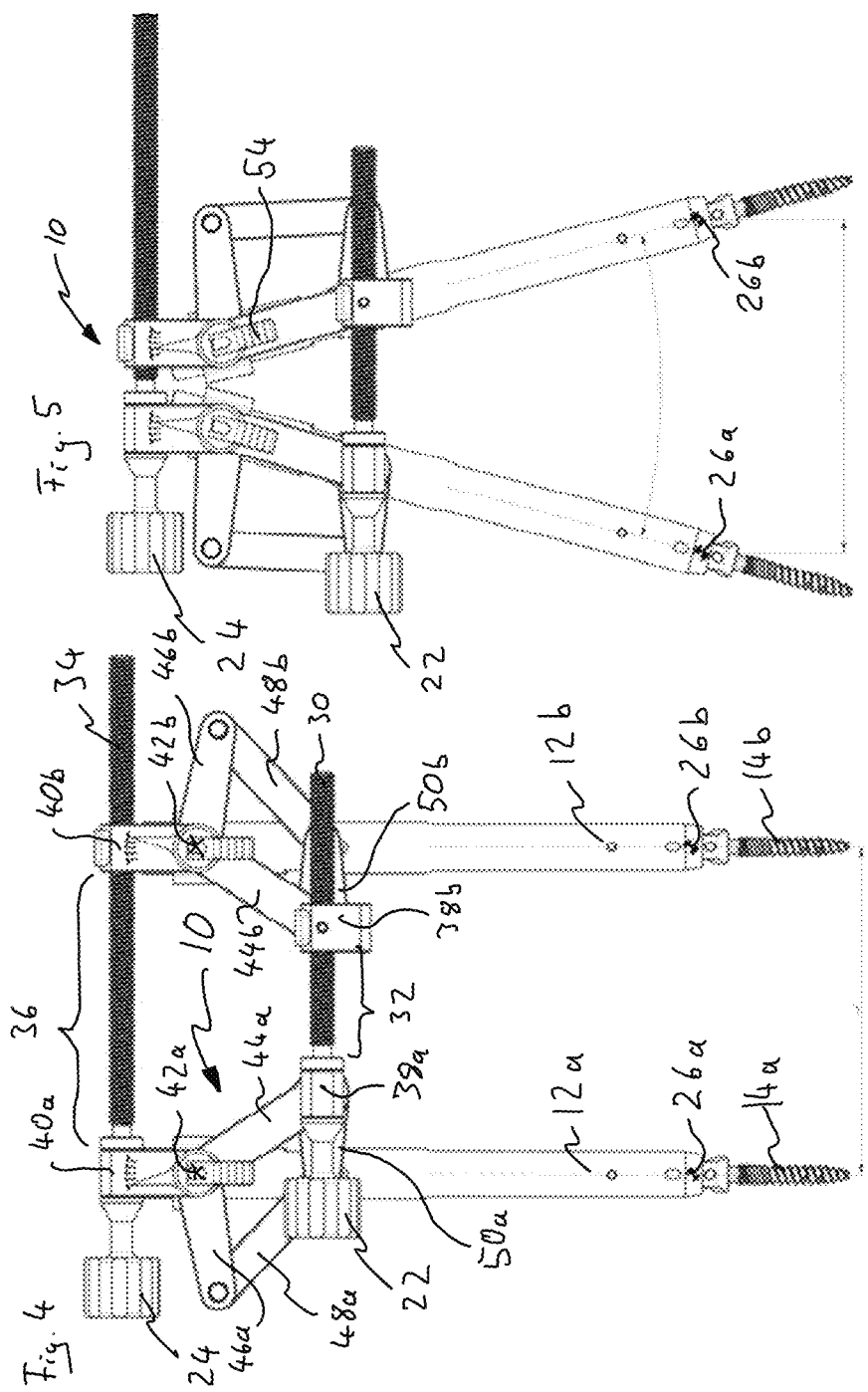

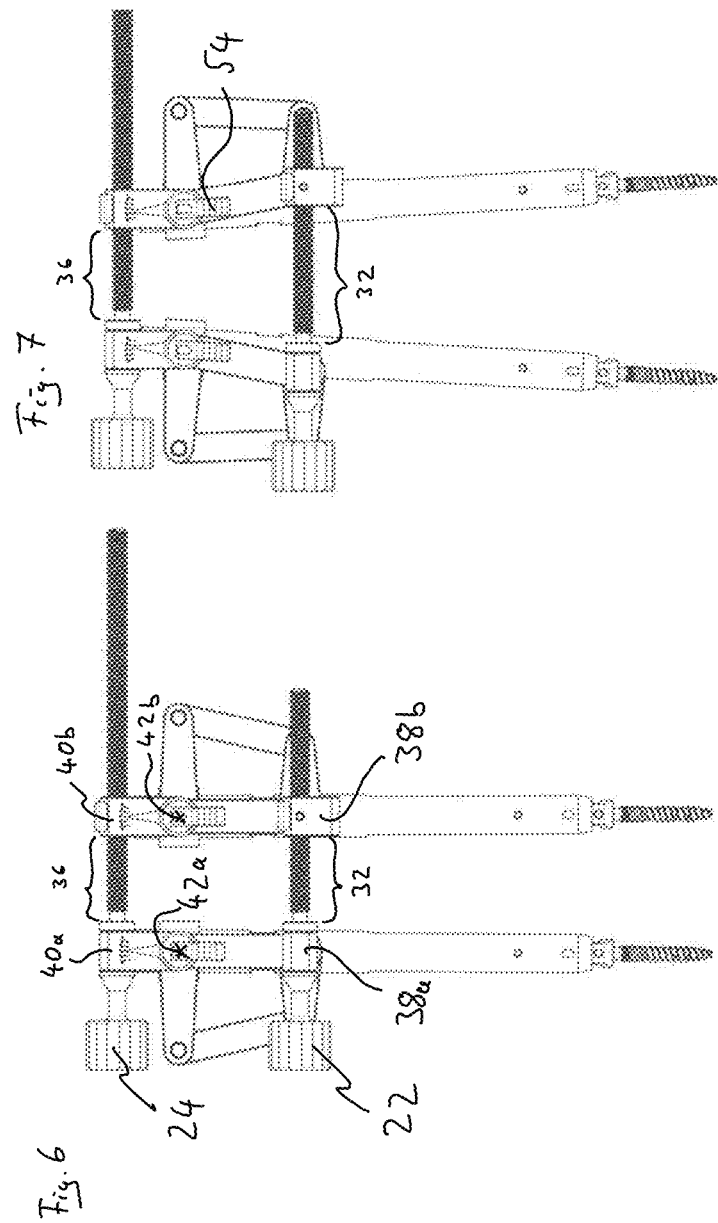

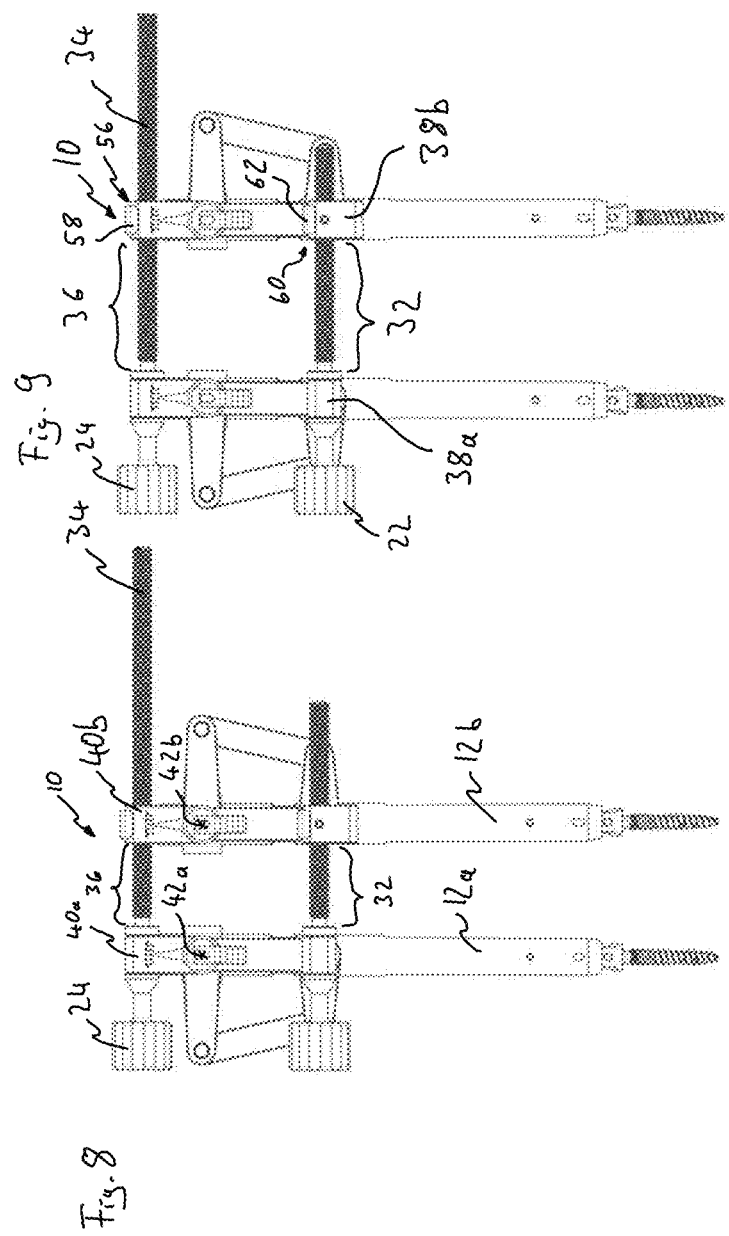

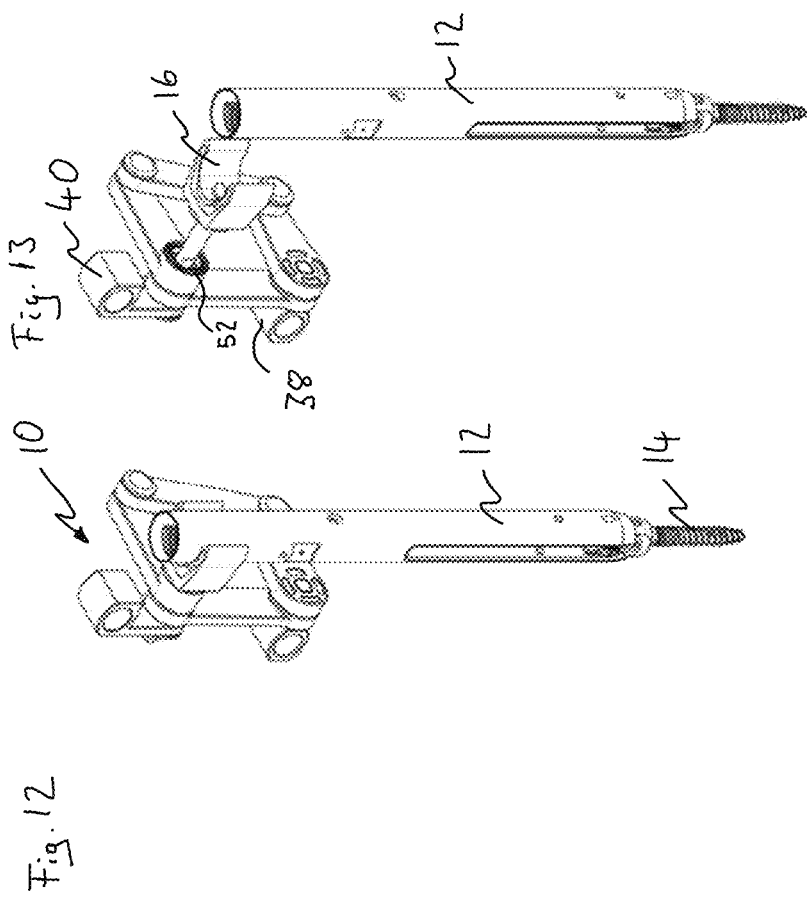

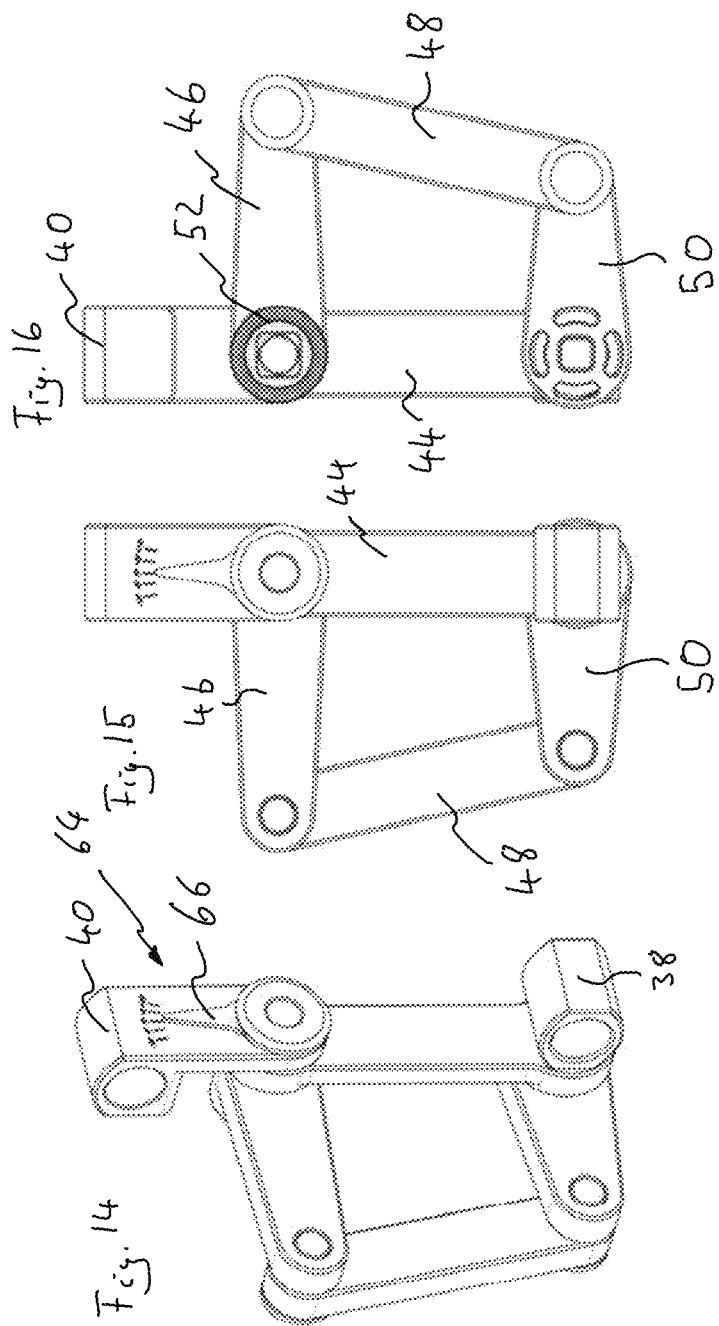

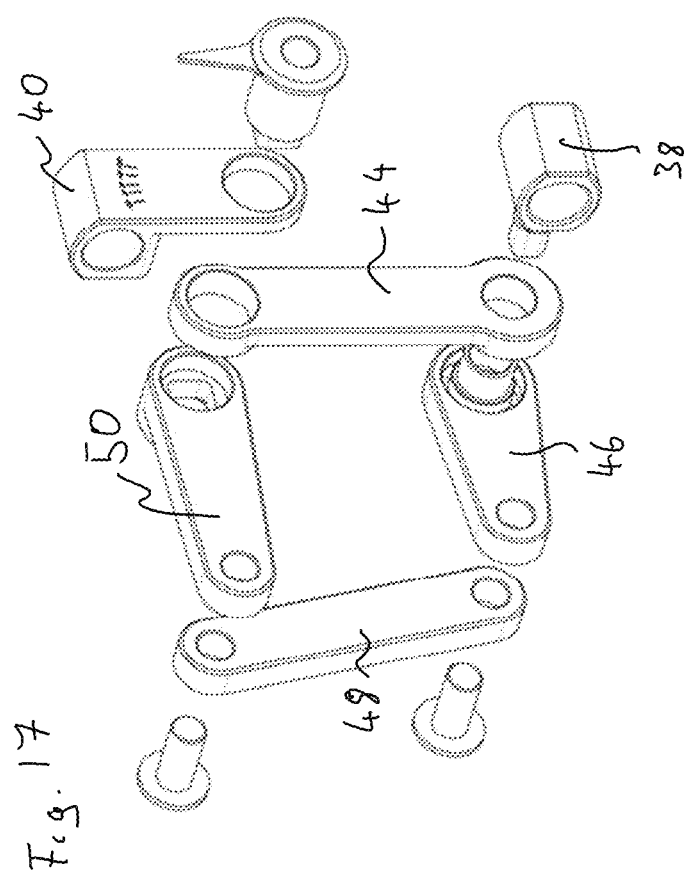

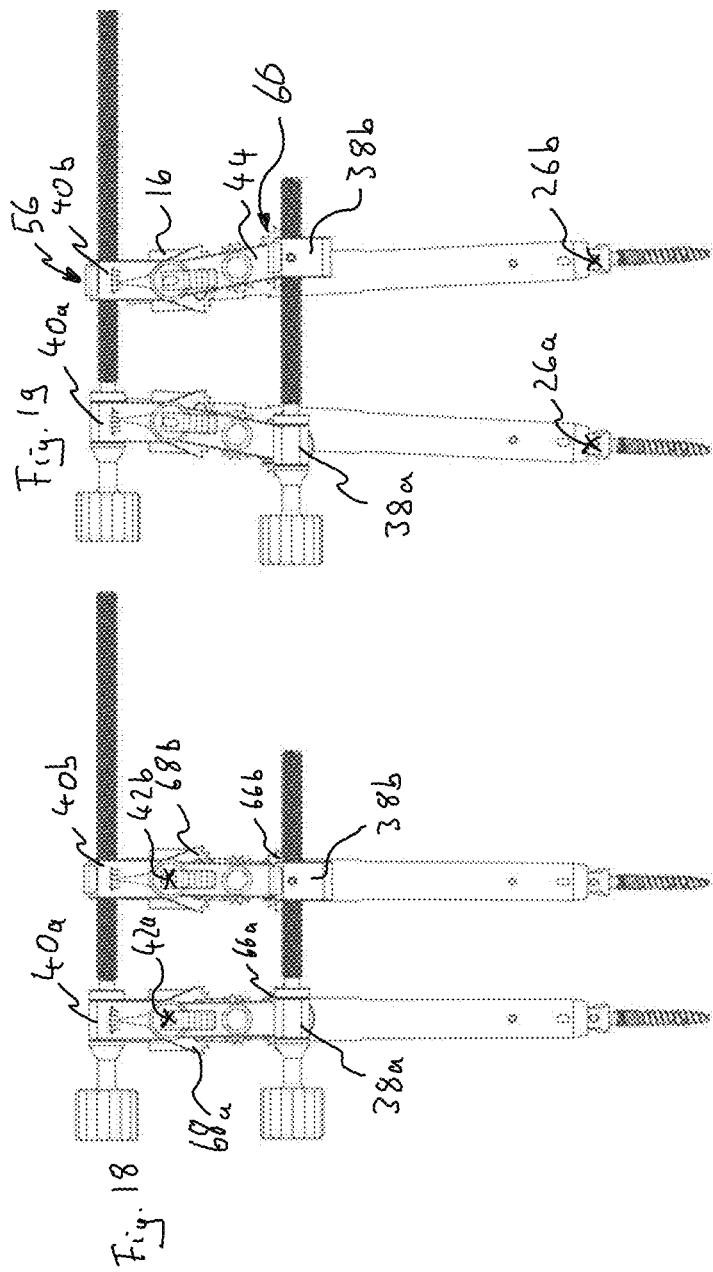

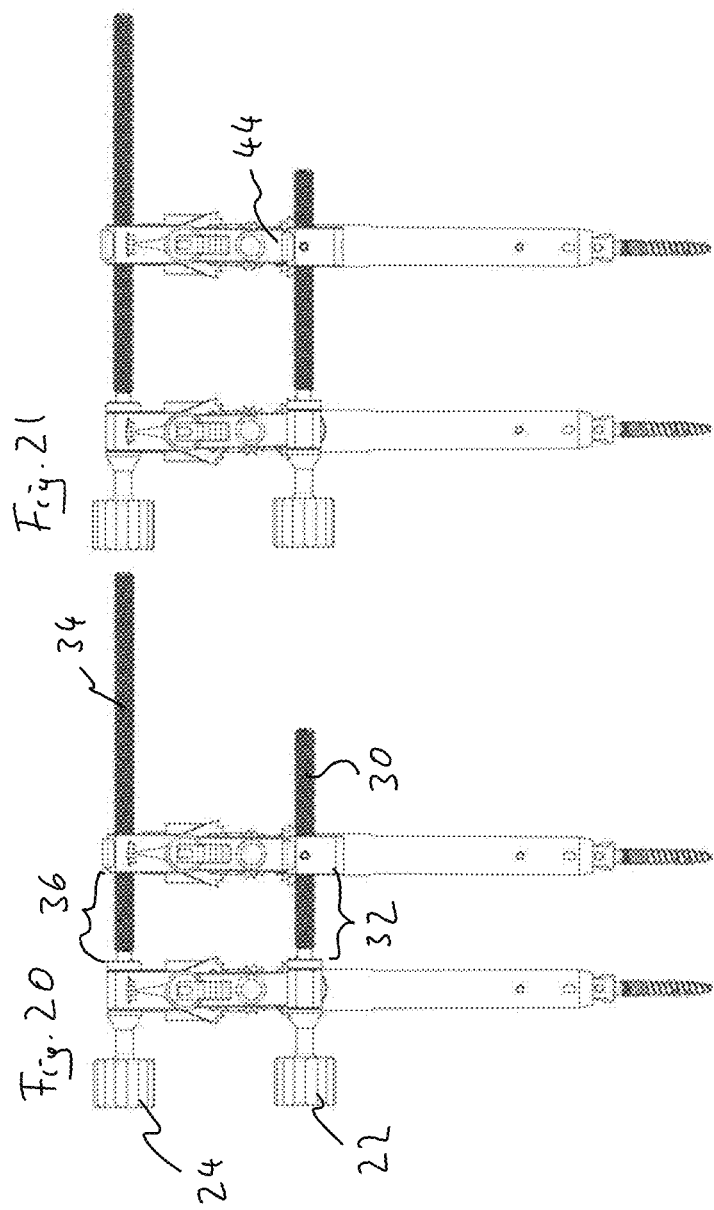

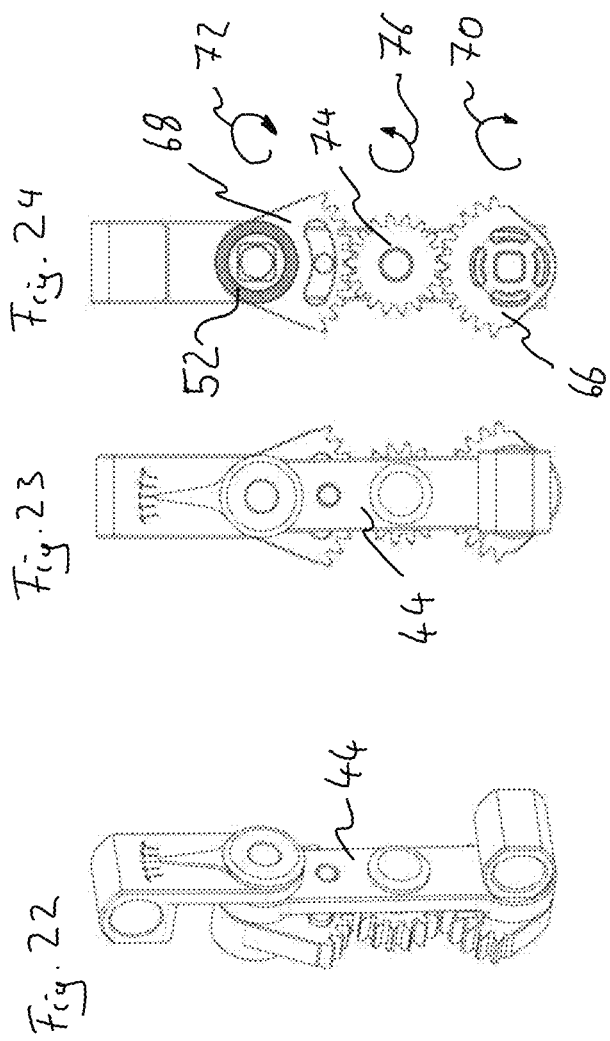

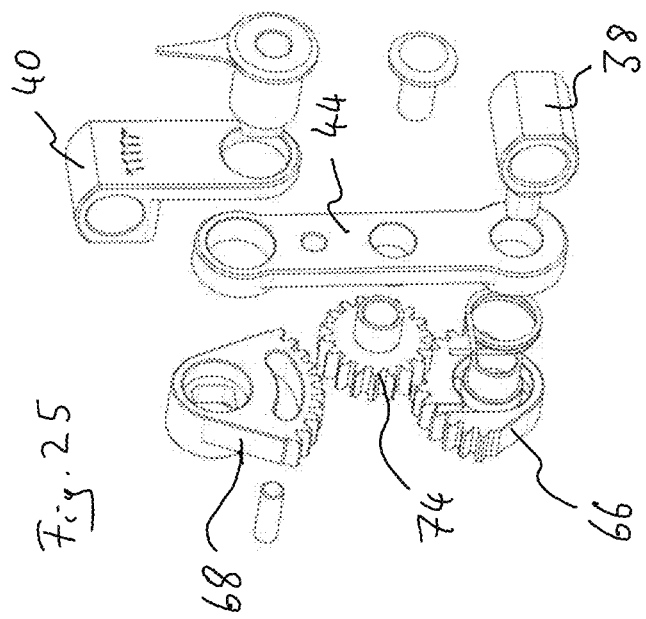

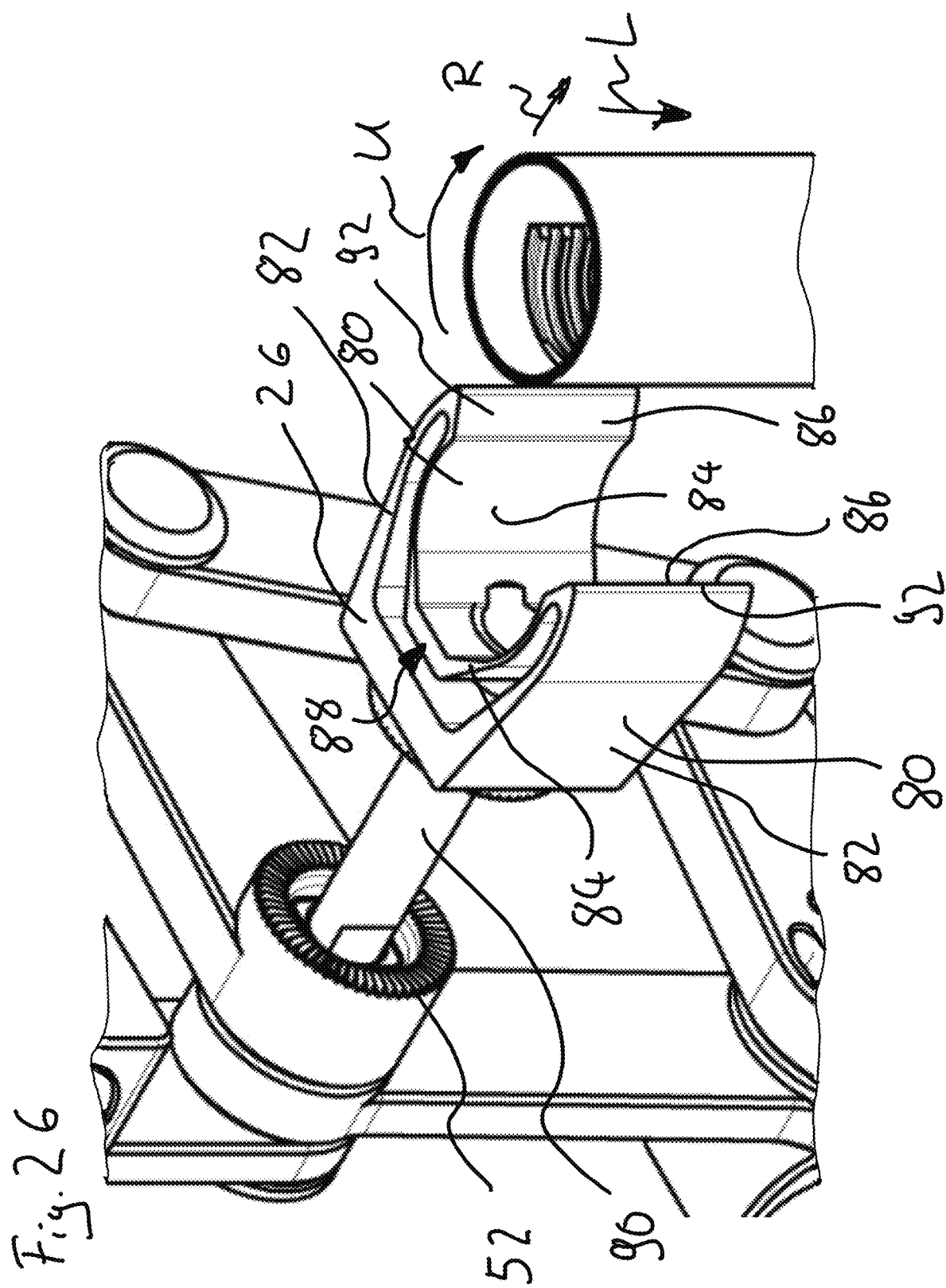

DEVICE FOR CORRECTING BONE FRACTURES

CROSS-REFERENCE TO RELATED APPLICATION

The present application is the U.S. National Stage Application of International Application No. PCT/EP2019/067967 filed Jul. 4, 2019, which relates and claims priority to German Application No. 10 2018 116 177.8, filed Jul. 4, 2018, the entire contents of each of which are hereby incorporated by reference.

BACKGROUND

The present invention relates to a device for correcting bone fractures, the device being designed so that the correction of the bone fracture is performed using bone anchors, in particular bone screws, in particular monoaxial bone screws or polyaxial bone screws, which can be temporarily blocked in their polyaxiality, and on extension devices attachable to the bone screws.

A polyaxial screw is known, for example, from U.S. Pat. No. 6,063,090. In the case of polyaxial screws, a fork head is attached so that it can pivot relative to a screw anchor. The screw anchor can be fixed in its position with respect to the fork head using appropriate devices. A monoaxial pedicle screw has a screw anchor which has a fork head as an extension in the proximal direction. The device according to the invention is particularly suitable for use with a bone anchor which is designed to produce a location-fixed and orientation-fixed connection to a bone segment. This can be realized, for example, with monoaxial bone anchors or with movable (polyaxial) bone anchors, which, however, can be fixed in a specific orientation.

An extension device in the present sense is a device which is elongated along one direction of a longitudinal extension and which is attached to the bone screw, for example on the fork head, and by means of which a lever is provided for pivoting the bone screw or the fork head. Extension devices in this sense can also be part of the system according to the invention and which will be explained later. The extension device, however, usually serves not only as a lever arm, but also to insert a correction rod into the fork head, for example. In particular, the extension device(s) can be designed as a tube, in particular along its longitudinal extent, laterally slotted singly or at several points distributed around the circumference. For example, one or more lateral slots can extend from the end provided for connection to the bone screw along the longitudinal extension, the slots preferably not extending over the entire longitudinal extension. However, it is conceivable that, for example, a slot extends over the entire longitudinal extent. However, an extension device can also comprise two "half-shell-like" elements that are independent of one another. Preferably, however, the extension device is designed essentially tubular.

SUMMARY OF THE INVENTION

The object of the present invention is to provide a device which is suitable for manipulating bone screws with extension devices attached to them in a controlled manner, wherein the device can be attached to the extension devices as advantageously as possible.

This object is achieved according to the invention by a device, a system consisting of a device according to the invention and two extension devices, in particular and two bone anchors, in particular polyaxial screws.

The device comprises a first receptacle and a second receptacle. The first receptacle is designed and arranged to receive a first extension device for a first bone screw. The first receptacle is also designed and arranged to form a first force introduction section into the first extension device. Forces, via which the position of the first extension device can be influenced, can be introduced into the extension device via the first receptacle. For example, the extension device can be pivoted by this introduction of force. The second receptacle is in turn designed and arranged to receive a second extension device for a second bone screw. The second receptacle is also designed and arranged to form a second force introduction section into the second extension device. Forces, via which the position of the second extension device can be influenced, can be introduced into the extension device via the second receptacle. For example, the extension device can be pivoted by this introduction of force.

The device comprises a first actuating device and a second actuating device. The device is designed in such a way that the first extension device has a first upper pivot axis provided and a first lower pivot axis provided at a distance from this and the second extension device has a second upper pivot axis provided and a second lower pivot axis provided at a distance from this when the extension devices are received in the receptacles in the provided positions.

The first actuating device is designed to move the first extension device and the second extension device to one another when actuated such that a distance between the first lower pivot axis and the second lower pivot axis changes. It can be provided in particular that the change in the distance is effected by pivoting the first extension device about the first upper pivot axis and the second extension device about the second upper pivot axis. In other words, when the first actuation device is actuated, both extension devices pivot about their respective upper pivot axes. When the first actuating device is actuated alone, the distance between the upper pivot axes remains the same and only the distance between the lower pivot axes changes.

The second actuating device is designed to pivot the first extension device about the first lower pivot axis and the second extension device about the second lower pivot axis when it is actuated. In other words, when the second actuating device is actuated, both extension devices pivot about their respective lower pivot axes. When the second actuating device is actuated alone, the distance between the lower pivot axes remains the same and only the distance between the upper pivot axes changes.

The first force introduction section is at a distance from one of the first pivot axes, in particular from the first lower pivot axis, in the direction of the longitudinal extension of the first extension device (based on its intended position when it is received in the receptacle) and the second force introduction section is spaced from one of the second pivot axes, in particular to the second lower pivot axis, in the direction of the longitudinal extent of the second extension device when the extension devices are received in the receptacles in the provided positions. In other words, when looking in the direction of the longitudinal extension of the respective extension device, the respective force introduction section and one of the respective pivot axes, in particular the lower pivot axis, lie behind one another at a distance from one another. To put it another way, the receptacles are located along the longitudinal extent of the extension devices at a different location on the extension device than one of the pivot axes; the receptacles are preferably arranged at a distance from the lower pivot axis. The upper pivot axis preferably extends through the receptacles and the lower pivot axis is spaced apart from the receptacles. The extension devices are preferably not contacted by any part of the device in the area of the lower pivot axes.

As a result, the device can be attached to the extension devices in a particularly simple and convenient manner. In particular, when the force introduction sections are spaced apart from the lower pivot axes, this offers the surgeon particularly good accessibility to the surgical site. The entire device can be arranged at a distance from the surgical site, which is typically very close to the lower pivot axes.

The device can also be described as follows:

Device for correcting a bone fracture using bone anchors, in particular bone screws, and extension devices that can be attached to the bone anchors, wherein the device comprises a first receptacle and a second receptacle, wherein the first receptacle is designed and arranged to receive a first extension device for a first bone anchor in a provided position in the receptacle and to form a first force introduction section into the first extension device, and wherein the second receptacle is designed and arranged to receive a second extension device for a second bone anchor in a provided position in the receptacle and to form a second force introduction section into the second extension device, wherein the device comprises a first actuating device and a second actuating device, wherein the device is designed such that the first extension device in the provided position has a first upper pivot axis provided and a first lower pivot axis provided at a distance therefrom and the second extension device in the provided position has a second upper pivot axis provided and a second lower pivot axis spaced from this, when the extension devices are received in the provided positions in the receptacles, wherein the first actuating device is designed to move the first extension device and the second extension device to each other when actuated in such a way that a distance between the first lower pivot axis and the second lower pivot axis changes, in particular the change in the distance by pivoting the first extension device is effected about the first upper pivot axis and the second extension device about the second upper pivot axis, and wherein the second actuating device is designed to pivot the first extension device about the first lower pivot axis and the second extension device about the second lower pivot axis when activated, characterized in that the first force introduction section formed by the first receptacle is spaced apart in the direction of the longitudinal extension of the first extension device from one of the first pivot axes, preferably the first lower pivot axis, and the second force introduction section formed by the second receptacle is spaced in the direction of the longitudinal extension of the second extension device from one of the second pivot axes, preferably the second lower pivot axis, when the extension devices are received in the provided positions in the receptacles and that the lower pivot axes are arranged in such a way that they are spaced apart from the extension devices in an extension of the longitudinal extent of these extension devices.

Accordingly, the device is designed to form a system with the extension devices, as will be discussed in detail later.

In the following, the individual aspects of the device and their possible configuration are discussed, and further possible embodiments of the device are described.

The receptacles are used to grasp the extension devices and to introduce the forces required to move or pivot the extension devices into them, since the receptacles form the force introduction sections.

The receptacles can, for example, be designed like clips. The receptacles can in particular be designed for detachable, in particular encompassing, clamping fastening to an outer circumference of the in particular rod-shaped or tubular extension devices that can be partially encompassed by means of the receptacles.

The first force introduction section formed by the first receptacle and the second force introduction section formed by the second receptacle can be the only force introduction sections in the extension devices. In other words, it is then provided that forces for movement, in particular for pivoting the extension devices, can be introduced into the extension devices by the device exclusively via these force introduction sections.

The pivot axes (upper and lower) can run orthogonally to the longitudinal direction or to the longitudinal extent of the extension devices.

In particular, the receptacles can be designed with a resiliently deflectable leg extending along a circumferential and longitudinal direction of the extension device, which leg can be placed from the outside on the outer circumference of the extension device, the at least one leg having an outer wall and an inner wall, which are connected to one another at at least one point in such a way that when pulling outer wall and inner wall against each other in the radial direction of the extension device, at a tension introduction point by means of a tension introduction mechanism, a compressive stress in the outer wall acting in the circumferential direction of the extension device starting from the tensile introduction point, and a tensile stress in the inner wall acting in the opposite circumferential direction is generated, whereby the leg is forced against the outer circumference of the extension device and the receptacle can thereby be arranged in a clamping manner on the extension device or the extension device can be gripped by the receptacle. This represents a particularly safe and comfortable design of the receptacles. It is also possible for only one of the receptacles to be designed as described above or below.

The receptacles (or a receptacle) are preferably designed in such a way that on both sides of the tension introduction point a resiliently deflectable leg extending in the circumferential direction and in the longitudinal direction of the extension device is provided, which leg can be placed on the outer circumference of the extension device, with each leg having an outer wall and an inner wall, which are connected to one another at at least one point in such a way that when pulling the outer wall and inner wall against each other in the radial direction of the extension device, at the tension introduction point by means of a tension introduction mechanism, a compressive stress in the outer wall acting in the circumferential direction of the extension device starting from the tension introduction point in the circumferential direction of the extension device, and a tensile stress acting in the opposite circumferential direction is generated in the inner wall of the respective leg, whereby the respective leg is forced against the outer circumference of the extension device and the receptacle can thereby be arranged in a clamping manner on the extension device.

The receptacles (or a receptacle) are preferably designed in such a way that the outer wall and the inner wall are connected to one another at least in the region of an end of the leg or legs which is free in the circumferential direction. In particular, the outer wall and the inner wall can merge into one another in one piece in the region of the free end of the leg or legs in the circumferential direction. It is also conceivable within the meaning of the invention that the outer wall and the inner wall of the receptacle are further connected to one another by additional struts or webs which, in the unloaded initial state of the receptacle, preferably extend essentially in a radial plane. The struts or webs can merge in one piece into the outer wall and/or into the inner wall.

The tension introduction mechanism of the receptacle can in particular be designed such that the inner wall can be moved or pulled in the direction of the outer wall in the region of the tension introduction point. For this purpose, the tension introduction mechanism can in particular comprise an eccentric adjusting device or a toggle lever adjusting device or a parallelogram gear.

Other types of receptacles, for example clamps that can be clamped by a screw mechanism, can also be used.

The lower and upper pivot axes of the extension devices are spaced apart from one another along the longitudinal direction of the extension device. The angular position of the extension device and thus the angular position of the bone screw can be changed by pivoting about the lower or upper pivot axis. A simultaneous pivoting about the upper and lower pivot axis of both extension devices can be used to bring about a translational movement of the extension devices with respect to one another. In particular, it is possible to move the extension devices in a translational manner relative to one another without changing the angular position of the extension device. The superimposed pivoting about both pivot axes can thus result, as it were, in a purely translational movement. With the device, for example, the distance between the two bone anchors can be adjusted and then the bone anchors can be pivoted about the respective pivot axes.

In particular, a parallel displacement of the extension devices with respect to one another can thus be achieved by means of the device. Such a parallel displacement is suitable, for example, for distracting bone segments around a fracture.

For example, the first bone screw to which the first extension device is attached can be inserted into a first intact vertebral bone of the spine and the second bone screw with the extension device attached to it can be inserted into a second vertebral bone of the spine, wherein a fractured vertebral bone is arranged between the first and second vertebral bones of the spine.

By parallel displacement of the extension devices and the bone screws attached to them by means of the device according to the invention, the fractured vertebral bone can be relieved and then treated.

By pivoting the extension device, the arrangement of the first and second vertebral bones can be modulated with respect to one another, for example corrected.

A corresponding method using the device according to the invention is also part of the present invention.

A method according to the invention comprises the steps:
Connecting a first extension device to the first bone anchor;
Inserting a first bone anchor into a first bone or section of bone;
Connecting a second extension device to the second bone anchor;
Inserting a second bone anchor into a second bone or section of bone;
Attaching a device according to the invention to the extension devices by receiving the extension devices in the corresponding receptacles;
Manipulating the position of the first bone or first bone section and of the second bone or second bone section with respect to one another using the device according to the invention.

The above-mentioned manipulation of the position preferably initially comprises manipulating the distance between the first bone or first bone section and the second bone or second bone section from one another using the device according to the invention. Such a manipulation of the distance can be achieved, for example, by actuating the first actuating device, which causes the extension device to pivot about the upper pivot axes and thus produces a change in the distance of the lower pivot axes. The distance can also be manipulated by actuating both actuating devices. Both actuating devices are preferably operated synchronously with one another in such a way that the change in distance between the lower pivot axes is caused by a parallel displacement (equal change in the distances between the upper and lower pivot axes) of the extension devices or the bone anchors connected to them. The change in distance between the lower pivot axes is transferred to the bone segments via the bone anchors.

This allows the distance between the bone segments to be set in a defined manner and kept constant. When treating a fracture, this can prevent further damage to the surrounding tissue, for example.

Preferably, the above-mentioned manipulation of the position after the above-mentioned manipulation of the distance comprises manipulating the pivot position of the bones or bone sections relative to one another, the pivot position being manipulated preferably while maintaining the constant distance between the lower pivot axes. the manipulation of the swivel position takes place by actuating the second actuating device. If the first actuating device is not actuated, the distance between the lower pivot axes remains constant and the extension devices or the bone anchor connected to them pivot about the respective lower pivot axis.

After setting the distance and/or the orientation of the bone segments with the aid of the device according to the invention, the bone anchors can be connected to one another with a connecting element (preferably a rod-shaped element) and fixed in their relative position and orientation to one another with the aid of connecting means (e.g. grub screws).

The device according to the invention can then preferably be removed from the extension devices.

Finally, the extension devices can preferably be decoupled from the bone anchors.

The device according to the invention can be designed in such a way that the first actuating device is designed to cause the pivoting movement about the change in distance between the lower pivot axes or the pivoting movement about the upper pivot axes by changing the length of a length-adjustable section of a first adjusting element, in particular a section of a first threaded rod. Alternatively or additionally, the second actuating device can be designed to bring about the pivoting movement about the lower pivot axes by changing the length of a length-adjustable section of a second adjusting element, in particular a section of a second threaded rod. This represents a simple way of designing the actuating devices.

In the device according to the invention it can be provided that the first adjusting element is mounted in a guide assigned to the first extension device and in a guide assigned to a second extension device. Here, the variable-length section of the first adjusting element can extend from the guide assigned to the first extension device to the guide assigned to the second extension device. By changing the length of the variable-length section, the guides can be moved with respect to one another, which in turn can be correspondingly coupled to the receptacles.

The guides are preferably designed in such a way that the variable-length sections of the first adjusting element are arranged displaceably in at least one of the guides. The first adjusting element preferably comprises a threaded section which is mounted in a guide-side thread in one of the guides. One of the guides, in particular the guide with the mating thread, preferably comprises a release mechanism by means of which the engagement of the guide-side thread into the adjusting element-side thread can be released so that the first adjusting element can be moved in the guide without screwing in the thread. The adjusting element is preferably mounted in the other, non-thread-bearing guide so that it can be moved in a purely rotational manner (that is, it is fixed in a translational manner with respect to the guide).

In the device according to the invention it can be provided in particular that the second adjusting element is mounted in the further guide assigned to the first extension device and a further guide assigned in the second extension device and the variable-length section of the second adjusting element extends from the further guide assigned to the first extension device to further guide assigned to the second extension device.

The further guides are preferably designed such that the variable-length sections of the second adjusting element are arranged displaceably in at least one of the further guides. The second adjusting element preferably comprises a threaded section which is mounted in a guide-side thread in one of the further guides. One of the further guides, in particular the further guide with the mating thread, preferably comprises a release mechanism by means of which the engagement of the guide-side thread into the adjusting element-side thread can be released so that the second adjusting element can be displaced in the further guide without screwing in the thread. The adjusting element is preferably mounted in the other, non-thread-bearing further guide so that it can be moved in a purely rotational manner (that is, it is fixed in a translational manner with respect to the guide).

In the device according to the invention, it can be provided in particular that the guide assigned to the first extension device can be pivoted about the first receptacle and that the guide assigned to the second extension device can be pivoted about the second receptacle.

In the device according to the invention it can also be provided that a guide (for example the first) is arranged at a distance from the corresponding (i.e. the first) receptacle in a plane orthogonal to the corresponding (i.e. the first) upper pivot axis. It can further be provided that the guide is connected to the receptacle via a corresponding connecting element. In particular, the connecting element can be inherently rigid. In particular, the connecting element can be pivotable with respect to the corresponding receptacle and with respect to the corresponding guide. In particular, the connecting element can be elongated and designed to run orthogonally to the corresponding upper pivot axis. In particular, it can be provided that both guides are spaced apart and connected to the respective receptacles in this way. It can be provided that the guide assigned to the first extension device is arranged at a distance from the first receptacle, in particular and is connected to the latter via an inherently rigid first connecting element pivotable with respect to the receptacle and with respect to the guide, and that the guide assigned to the second extension device is arranged at a distance from the second receptacle, in particular and is connected to the latter via an inherently rigid second connecting element, which is pivotable relative to the receptacle and relative to the guide.

In particular in combination with the connecting element, it can be provided in the device according to the invention that a receptacle-side arm is arranged non-rotatably opposite one of the receptacles and extends from the receptacle to a coupling element which is spaced from the receptacle and pivotally connected to the arm and which in turn is pivotably connected to a guide-side arm, which in turn extends from the pivotable connection with the coupling element to the guide and is non-rotatably arranged opposite this. In this way, the first receptacle can be connected to the first guide and/or the second receptacle to the second guide.

The non-rotatable connection between the receptacle and the receptacle-side arm and/or the non-rotatable connection between the guide and the guide-side arm can be temporarily detachable so that the angular position between the receptacle and the receptacle-side arm or between the guide and the guide-side arm is freely pivotable. This can be implemented, for example, by a toothing on the mutually facing sides of the receptacle-side arm and the receptacle or the guide-side arm and the guide. A bracing mechanism can be provided which can pull the toothings into one another and when it is loosened the toothings can be detached from one another so that the two parts can be freely moved or pivoted with respect to one another. Other detachable non-rotatable connections are conceivable.

Thus, for example, a first receptacle-side arm can be arranged in a non-rotatable manner opposite the first receptacle and can extend from the first receptacle to a first coupling element which is spaced from the first receptacle and is pivotably connected to the arm, which in turn is pivotably connected to a first guide-side arm, which in turn extends from the pivotable connection with the first coupling element to the first guide and is arranged non-rotatably relative to this. In this way, an efficient coupling can be achieved between the displacement of the guides and the adjusting elements and the angular position of the receptacles. The same applies to the connection between the second receptacle of the second guide.

It can be provided that the connecting element, the coupling element, the receptacle-side arm and the guide-side arm are arranged essentially in a common plane, in particular which runs orthogonally to the upper pivot axis. In one plane also means that the individual parts rest on one another, as can be seen, for example, in the following figures, but that the individual parts extend in this plane and do not extend out of the plane in the direction of the pivot axis.

It can also be provided that a guide is non-rotatably connected to a guide-side toothed section. The corresponding receptacle can be connected non-rotatably to a receptacle-side toothed section. In particular, the guide-side toothed section and the receptacle-side toothed section can be coupled in terms of movement such that the guide-side toothed section and the receptacle-side toothed section have co-rotating directions of rotation. In particular, the two toothed sections can be coupled in motion via a gear arranged between the guide-side toothed section and the receptacle-side toothed section, in particular that meshes with the guide-side toothed section and the receptacle-side toothed section, such that the guide-side toothed section and the receptacle-side toothed section have the same directions of rotation. Both guides can be connected to the respective receptacles in this way. It can be provided that the guide-side toothed section and the receptacle-side toothed section, in particular and the gear, are arranged essentially in a common plane, in particular which runs orthogonally to the upper pivot axis.

The respective guide can be connected to the guide-side toothed section via an inherently rigid connecting element, which can be pivoted relative to the corresponding receptacle and relative to the guide, to the corresponding receptacle. The connecting element can be elongated and arranged orthogonally to the corresponding upper pivot axis. The gear can be rotatably mounted on the connecting element.

The non-rotatable connection between the receptacle and the receptacle-side toothed section can be temporarily detachable. Likewise or alternatively, the non-rotatable connection between the guide and the guide-side toothed section can be temporarily detached. Correspondingly, the angular position between the receptacle and the receptacle-side toothed section or between the guide and the guide-side toothed section can be freely pivotable. In this way, for example, the coverage area of the angular area of the interleaving of the extension device with respect to one another can be increased.

In the context of the present invention, it is particularly important that the upper pivot axes extend through the receptacles.

Part of the present invention is also a device which, on one receptacle, has the connection to the guide by means of a connecting element, receptacle-side arm, coupling element and guide-side arm, and on the other receptacle has the connection to the guide by means of the toothed sections.

As already mentioned at the beginning, part of the invention is also a system comprising a device according to the invention and two extension devices, in particular and two bone anchors. In particular, the device is designed such that the lower pivot axes are located in the area of the extension devices in which the extension devices contact the bone anchors when they are attached to the bone anchors. It is also within the meaning of the invention when the lower pivot axes each extend through the bone anchors, when the extension devices with the bone anchors attached to them are received in the device, it being possible in particular for the pivot axes to extend outside the extension devices. The pivot axes preferably run through the fork head of the bone anchors, for example designed as polyaxial screws.

BRIEF DESCRIPTION OF THE DRAWINGS

Further details, features and advantages of the invention can be found in the attached claims and the drawings and the following description of a preferred embodiment of the invention.

In the drawing:

FIG. 1 shows an illustration of the device according to the invention;

FIG. 2 shows a perspective view of the device from FIG. 1;

FIG. 3 shows a further perspective view of the device from FIG. 1;

FIG. 4 shows a view of the device from FIG. 1 in a different position;

FIG. 5 shows a view of the device from FIG. 1 in a further position;

FIG. 6 shows a view of the device from FIG. 1 in a further position;

FIG. 7 shows a view of the device from FIG. 1 in a further position;

FIG. 8 shows a view of the device from FIG. 1 in a further position;

FIG. 9 shows a view of the device from FIG. 1 in a further position;

FIG. 12 shows a view of part of the device from FIG. 1;

FIG. 13 shows a view of the part from FIG. 12 in a partially exploded representation;

FIG. 14 shows a view of part of the device from FIG. 1;

FIG. 15 shows a further view of the part of the device from FIG. 14;

FIG. 16 shows a further view of the part of the device from FIG. 14;

FIG. 17 shows an exploded view of the part of the device from FIG. 16;

FIG. 18 shows an illustration of a further device according to the invention;

FIG. 19 shows a view of the device from FIG. 18 in a different position;

FIG. 20 shows a view of the device from FIG. 18;

FIG. 21 shows a view of the device from FIG. 18 in a further position;

FIG. 22 shows a view of part of the device from FIG. 18;

FIG. 23 shows a view of part of the device from FIG. 18;

FIG. 24 shows a view of part of the device from FIG. 18;

FIG. 25 shows a view of part of the device from FIG. 18; and

FIG. 26 shows a view of part of the device from FIG. 12.

DETAILED DESCRIPTION

Figure 11:
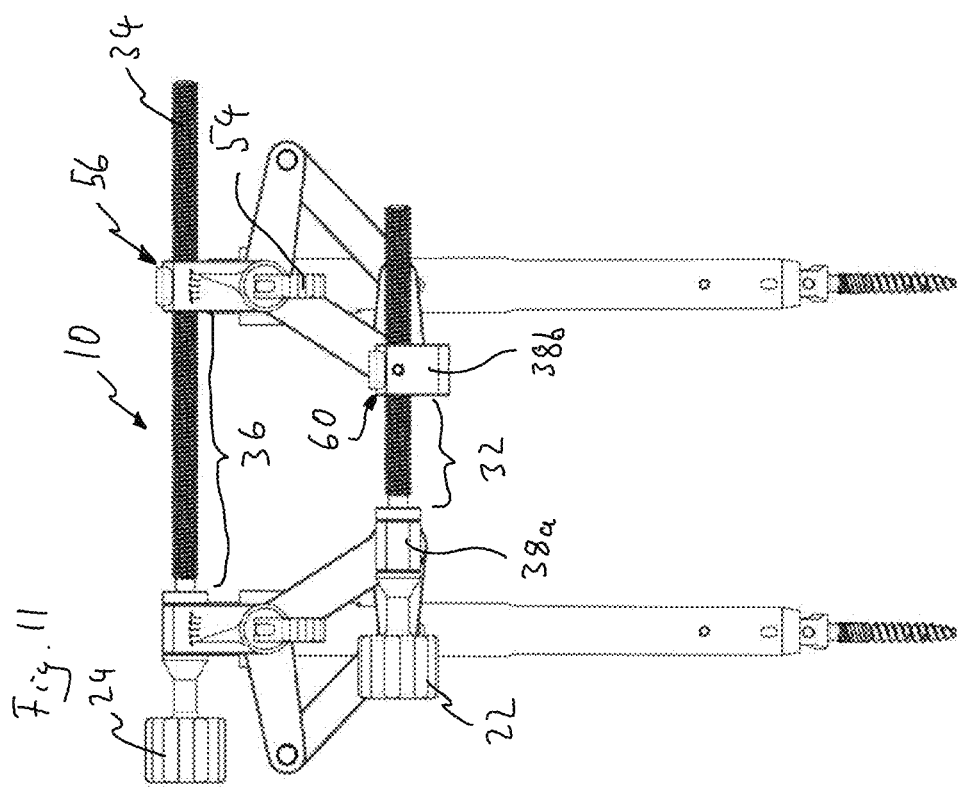
FIG. 11 shows a view of the device from FIG. 1 in a further position.

FIG. 1 shows a device 10 according to the invention, which is connected to a first extension device 12a and a second extension device 12b. The first extension device 12a is connected to a first bone screw 14a and the second extension device 12b is connected to a second bone screw 14b.

In FIGS. 2 and 3, the device 10 from FIG. 1 is shown in different perspective views. The device 10 has a first receptacle 16a in which the first extension device 12a is received. A second receptacle 16b, in which the second extension device 12b is received, is arranged at a distance from the first receptacle 16a. The receptacles 16 can be clearly seen in FIG. 2, for example.

The first receptacle 16a forms a first force introduction section into the first extension device 12a, the second receptacle 16b in turn forms a second force introduction section into the second extension device 12b.

The device 10 has a first actuation device 22 and a second actuation device 24. Via the second actuating device 24, the first extension device 12a and the second extension device 12b can each be pivoted about a first lower pivot axis 26a and a second lower pivot axis 26b, respectively. When the second actuating device 24 is actuated alone, the distance between the lower pivot axes 26 remains constant. The position of the lower pivot axes 26a can be clearly seen in FIG. 3. In the present example, the device 10 is designed in such a way that the lower pivot axes 26 is arranged in the area of the extension devices 12 in which the bone screws 14 are coupled to the extension devices 12. However, it is also conceivable, for example, that the lower pivot axis 26 are located quasi outside the extension devices 12. For example, it is possible for the lower pivot axis 26 to be arranged in the region of the transition between the fork head and the thread-bearing part of the bone screws 14. The pivoting about the lower pivot axis 26 is illustrated in FIGS. 4 and 3.

When actuating the actuating device 22, the first extension device 12a and the second extension device 12b can be moved relative to one another via the first actuation device 22 in such a way that a distance between the first lower pivot axis 26a and the second lower pivot axis 26b changes.

In the present case, the first extension device 12a and the second extension device 12b can each pivot about a first upper pivot axis 42a and a second upper pivot axis 42b via the first actuating device 22. The pivoting about the upper pivot axis 26 is illustrated in FIGS. 6 and 7. In the present case, the pivoting of the extension devices 12a and 12b about the upper pivot axes 42a and 42b causes a change in the distance between the lower pivot axes 26a and 26b. With this change in distance, the distance between the bone anchors 14a and 14b can be set in a defined manner. When the first actuating device 22 is actuated alone, the distance between the upper pivot axes 42 remains constant.

The pivoting movements shown in FIGS. 4 to 7 are carried out, as already explained, by actuating the first actuating device 22 or the second actuating device 24. The mechanism for performing the pivoting movements, which can be operated via the actuating devices 22, 24, is explained below.

The first actuating device 22 is connected to a first adjusting element 30 which has a length-adjustable section 32. In the present case, the first adjusting element 30 is designed as a threaded rod.

The second actuating device 24 is connected to a second adjusting element 34, which has a length-adjustable section 36. The second adjusting element 34 is designed as a threaded rod in the present embodiment.

The first adjusting element 30 is mounted in a guide 38a assigned to the first extension device 12a and in a guide 38b assigned to the second extension device 12b, which has an internal thread.

The variable-length section 32 of the first adjusting element 30 extends from the guide 38a assigned to the first extension device 12a to the guide 38b assigned to the second extension device 12b.

The second adjusting element 34 is mounted in a further guide 40a assigned to the first extension device 12a and in a further guide 40b assigned to the second extension device 12b.

The variable-length section 36 of the second adjusting element 34 extends from the further guide 40a assigned to the first extension device 12a to the further guide 40b assigned to the second extension device 12b.

A first connecting element 44a extends from the first receptacle 16a to the guide 38a assigned to the first extension device 12a. Correspondingly, a second connecting element 44b extends from the second receptacle 16b to the guide 38b assigned to the second extension device 12b. The respective connecting elements 44a and 44b are inherently rigid.

The connecting elements 44a and 44b are each connected to a first and second coupling element 48a and 48b via a first receptacle-side arm 46a and a second receptacle-side arm 46b, the respective coupling element 48a and 48b extending from the connection point with the respective receptacle-side arm 46a or 46b extends to a connection point with a respective first or second guide-side arm 50a or 50b.

The respective connecting elements 44a and 44b are pivotable about the respective guides 38a and 38b as well as the receptacles 16a and 16b. The receptacle-side arms 46, coupling elements 48 and guide-side arms 50 are each pivotably connected to one another and pivotably connected to the respective connecting element 44.

The receptacle-side arms 46 are connected to the respective receptacles 16 for rotation therewith. The guide-side arms 50 are in turn connected to the guides 38 in a non-rotatable manner.

Due to the arrangement of the connecting elements 44, the receptacle-side arms 46, the coupling elements 48, and the guide-side arms 50, the guides 38 and the further guides 40 are coupled to the receptacles 16. As a result of this coupling, a respective pivoting movement of extension devices 12 about the lower and upper pivot axes 26 and 42 can be brought about by changing the distance between the guides 38 or the further guides 40. The pivoting movement is brought about by a corresponding introduction of force via the receptacles 16 into the extension devices 12.

In the present case, the actuating devices 22 and 24 are designed in such a way that the adjusting elements 30 and 34 can be rotated by rotating the actuating device 22 and 24. The adjusting elements 30 and 34 are mounted in the guide 38a assigned to the first extension device 12a and in the further guide 40a so as to be rotatable but held in a translational manner. In the guide 38b assigned to the second extension device 12b and the further guide 40b, the first adjusting element 30 and the second adjusting element 34 can be mounted rotatably in a thread integrated in the guide 38b or further guide 40b and displaceable translationally relative to the guide 38b or further guide 40b (by screwing in the thread).

When the adjusting elements 30 or 34 are rotated via the actuating device 22 or 24, the adjusting elements 30 or 34 screw into the thread of the guide 38b or further guide 40b. As a result, the distance between the guides 38a and 38b or further guides 40a and 40b which are assigned to the first and second extension devices 12a and 12b is changed in each case. In other words, the variable-length section 32 of the first adjusting element 30 is changed as a result, so that the distance between the guide 38a assigned to the first extension device 12a and the guide 38b assigned to the second extension device 12b is changed.

Correspondingly, when the adjusting element 34 is screwed into the thread of the further guide 40b, the length of the variable-length section 36 of the second adjusting element 34 and thus the distance between the further guide 40a assigned to the first extension device 12a and the further guide 40b assigned to the second extension device 12b is changed.

It can be provided in the devices according to the invention that a stabilization device is provided which is designed and arranged in such a way that the adjusting elements 30 and 34 are always held in a parallel alignment by the stabilization device. For example, the stabilization device can comprise two stabilization guides through which an adjusting element 30, 34 extends, these stabilization guides being connected to one another in such a way that the adjusting elements 30, 34 must always aligned parallel to one another.

In the present example, the upper pivot axes 42 extend through the respective receptacles 16. During pure pivoting about the upper pivot axes 42 (FIGS. 6 and 7), only the receptacles 16 rotate. This is achieved by the above-described change in length of the variable-length section 32 of the first adjusting element 30 while the length of the variable-length section 36 of the second adjusting element 34 remains the same. The change in the distance between the guide 38a assigned to the first extension device 12a and the guide 38b assigned to the second extension device 12b causes the receptacles 16 to rotate, their distance being kept constant via the rotatable connection of the respective further guide 40 to the corresponding receptacle 16. The change in distance between the guides 38 is converted into the rotation of the receptacles via the coupling with the receptacles by means of the connecting elements 44, the receptacle-side arms 46, the coupling elements 48, and the guide-side arms 50.

When they are simply pivoted about the lower pivot axes 26 (FIGS. 4 and 5), the receptacles 16 rotate and move away from one another or toward one another. In the present case, this is achieved by changing the length of the variable-length section 36 of the second adjusting element 34 as described above while the length of the variable-length section 32 of the first adjusting element 30 remains the same. The change in the distance between the further guides 40 is transmitted to the receptacles 16 by their rotatable coupling. The distance between the guides 38, which is kept constant during this change in distance and which are in turn coupled to the receptacle 16 via the connecting element 44, the receptacle-side arm 46, the coupling element 48 and the guide-side arm 50, leads to the rotation of the receptacles 16, which is superimposed on their change in distance. With this movement, the distance between the lower pivot axes 26a and 26b is kept constant.

If both actuation devices 22 and 24 are actuated at the same time, the extension devices 12a and 12b can be moved toward or away from one another without causing pivoting. Such a parallel displacement of the extension devices 12 is illustrated in FIGS. 8 and 9. The device 10 of the present example is designed in such a way that if the change in length of the two length-adjustable sections 32 and 36 of the adjusting elements 30, 34 differs, the extension devices 12a and 12b pivot about the corresponding pivot axes. This pivoting can be superimposed on the parallel displacement of the extension devices 12.

In FIGS. 12 and 13, part of the device 10 with an extension device 12 is shown individually. In FIG. 12, the non-rotatable connection between the receptacle-side arm 46 and the receptacle 16 is clearly visible. In the present case, the non-rotatable connection is implemented via a toothing 52 on the side of the receptacle-side arm 46 and a corresponding toothing on the side of the receptacle (see also FIG. 16 in this regard).

In FIGS. 14 to 16, the arrangement of the connecting elements 44, the receptacle-side arms 46, the coupling elements 48 and the guide-side arms 50 is shown again in detail and shown in FIG. 17 in an exploded view.

The device 10 has a detachment mechanism 54. The engagement of the toothing 52 on the side of the receptacle-side arm 46 with the receptacle 16 can be detached via the detachment mechanism 54, so that the non-rotatable connection between the receptacle-side arm 46 in the receptacle 16 can be temporarily detached, so that the receptacle 16 with respect to the receptacle-side arm 46. As a result, the position of the receptacle 16 relative to the receptacle-side arm 46 can be freely changed, whereby the pivot position of the extension device 12 can be adjusted without operating the actuating devices 22 and 24. In order to indicate a pivoting of the receptacle 16 relative to the neutral position by detaching the non-rotatable connection with the receptacle-side arm 46, the device 10, as in the present example, can have a display device 64, for example comprising a pointer 66 non-rotatably connected to the receptacle-side arm 46.

A detachment mechanism 54 can also be arranged in the area of the connection between the guide 38 and the guide-side arm 50 in order to temporarily detach their non-rotatable connection.

The second guide 38b and the second further guide 40b each have a release mechanism 56 and 60, which can each be actuated via a push button 58 or 62.

In the second guide 38b and the second further guide 40b, the first adjusting element 30 and the second adjusting element 34 are each arranged such that their thread engages a guide-side thread. When the release mechanism 56 or 60 is actuated, the engagement of these threads is detached and the respective adjusting element 30 or 34 is freely translationally movable in the guide 38b or further guide 40b.

Figure 10:
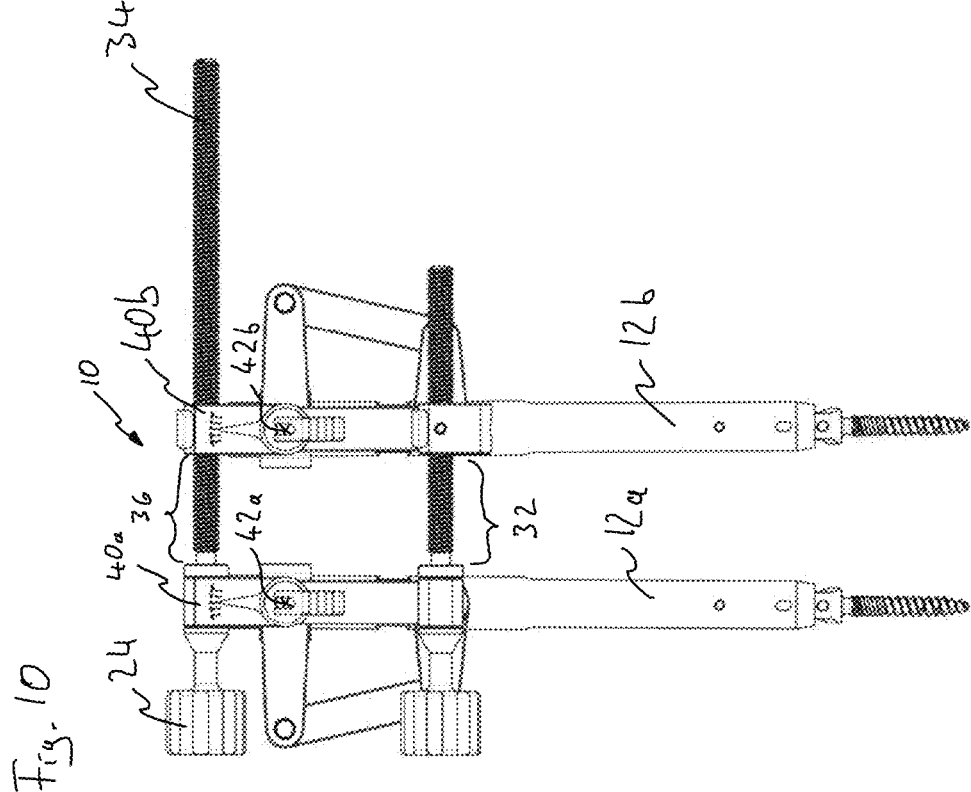
FIG. 10 shows a view of the device from FIG. 1 in a further position.

By releasing the release mechanism 56 and the detachment mechanism 54, the device 10 can be transferred from the position shown in FIG. 10 into the position shown in FIG. 11 without the actuating devices 22, 24 needing to be actuated.

In clinical application, the device 10 can be used, for example, as follows: In the case of a fractured vertebral body, the distance between the bone screws 14 or pedicle screws that are introduced into the adjacent vertebral bodies can first be set in a defined manner (compression/distraction). The pivoting position of the extension devices can then be changed without changing the distance between the bone anchors or pedicle screws. This allows a fractured vertebral body, which has mostly experienced a wedge fracture, to be straightened up again.

FIG. 18-21 show a further embodiment of the device 10 according to the invention.

In this embodiment, the guides 38 are each non-rotatably connected to a guide-side toothed section 66. The receptacles 16 are each connected non-rotatably to a receptacle-side toothed section 68. This non-rotatable connection is in the present case designed to be detachable via a detachment mechanism 54. Similar to the previous embodiment, the non-rotatable connection is formed by a toothing 52 which can be brought into engagement with a toothing on the receptacle 16. The toothing 52 is arranged on the receptacle-side toothing section 68 and on the receptacle. Correspondingly, in the detached state, the angular position between the receptacle 16 and the toothed section 68 on the receptacle can be freely pivoted.

The non-rotatable connection of the guide 38 to the guide-side toothed section 66 can also be designed to be detachable via a detachment mechanism. Accordingly, in the detached state, the angular position between the guide 38 and the guide-side toothed section 66 is freely pivotable.

The guide-side toothed section 66 and the receptacle-side toothed section 68 are coupled in terms of movement to one another such that the guide-side toothed section 66 and the receptacle-side toothed section 68 have co-rotating directions of rotation 70 and 72. The direction of rotation illustrated by the arrows in FIG. 25 is only to be understood as an example. The rotation can also take place in the opposite direction, in which case it is then also in the same direction for the guide-side toothed section 66 and the receptacle-side toothed section 68. The movement coupling is implemented in the present case via a gear 74 arranged between the guide-side toothed section 66 and the receptacle-side toothed section 68. The gear 74 has a direction of rotation 76 which is opposite to the directions of rotation 70 and 72 of the toothed sections 66 and 68 and is in engagement with the toothed sections 66 and 68.

The guides 38 with the respective guide-side toothed sections 66 are each connected to the corresponding receptacle 16 via an inherently rigid connecting element 44 that is pivotable relative to the respective receptacle 16 and relative to the respective guide 38. The connecting element 44 is designed similar to the connecting element 44 of the previous embodiment, extends elongated and is arranged orthogonally to the respective upper pivot axis 42.

The gear 74 is rotatably mounted on the connecting element 44.

Otherwise, the device 10 of FIG. 18-25 is constructed similarly to the previous embodiment and also has a first actuating device 22 and a second actuating device 24 as well as a corresponding first adjusting element 30 and a second adjusting element 34 with corresponding length-adjustable sections 32 and 36.

The receptacles 16 are formed with two resiliently deflectable legs 80 which extend along a circumferential direction U and longitudinal direction L of the extension device 12 and which can be applied from the outside to the outer circumference of the extension device 12 (see FIG. 26, which shows a portion of FIG. 13 enlarged).

The legs each have an outer wall 82 and an inner wall 84. The outer wall 82 and the inner wall 84 are connected to each other in each of the legs 80 at at least one point 86 (in this case the circumferential end of the legs) so that when the outer wall 82 and inner wall 84 are pulled against one another in the radial direction R of the extension device 12 at a tension introduction point 88 by means of a tension introduction mechanism 90, a compressive stress in the outer wall 82 acting in the circumferential direction U of the extension device 12 starting from the tensile introduction point 88 and a tensile stress acting in the opposite circumferential direction U in the inner wall 84 are generated, whereby the respective leg 80 is forced against the outer circumference of the extension device 12 and thereby the receptacle 16 can be arranged in a clamping manner on the extension device 12 or the extension device 12 can be gripped by the receptacle 16 in a clamping manner. The connection of outer wall 82 and inner wall 84 is realized in the present case in the area of an end 92 of the respective leg which is free in the circumferential direction U. For this purpose, the outer wall 82 and the inner wall 84 merge in one piece with one another in the area of the free end 92 of the leg 80 or the legs 80 in the circumferential direction U.

In the present case, the receptacles 16 are designed such that a resiliently deflectable leg 80 extending in the circumferential direction U and in the longitudinal direction L of the extension device is provided on both sides of the tension introduction point 88.

The invention claimed is:

1. A device for correcting bone fractures using bone anchors and extension devices attachable to the bone anchors,
   wherein the device comprises a first receptacle and a second receptacle,
   wherein the first receptacle is designed and arranged to receive a first extension device for a first bone anchor and to form a first force introduction section into the first extension device, and
   wherein the second receptacle is designed and arranged to receive a second extension device for a second bone anchor and to form a second force introduction section into the second extension device,
   wherein the device comprises a first actuating device and a second actuating device,
   wherein the device is designed such that the first extension device has a first upper pivot axis provided and a first lower pivot axis provided at a distance from this and the second extension device has a second upper pivot axis provided and a second, lower pivot axis provided at a distance from this, when the extension devices are received in the receptacles,
   wherein the first actuating device is designed to move, when actuated, the first extension device and the second extension device to one another in such a way that a distance between the first lower pivot axis and the second lower pivot axis changes, wherein the change in the distance is caused by pivoting the first extension device about the first upper pivot axis and the second extension device about the second upper pivot axis, and
   wherein the second actuating device is designed to pivot the first extension device about the first lower pivot axis and the second extension device about the second lower pivot axis when actuated,
   wherein, the first force introduction section formed by the first receptacle is spaced apart in the direction of the longitudinal extent of the first extension device from one of the first pivot axes, and that the second force introduction section formed through the second receptacle is spaced in the direction of the longitudinal extension of the second extension device to one of the second pivot axes when the extension devices are received in the receptacles,
   wherein the first receptacle is designed and arranged such that forces, via which the first extension device can be pivoted about the first upper pivot axis, and forces, via which the first extension device can be pivoted about the first lower pivot axis, can be introduced into the first extension device via the first receptacle and wherein the second receptacle is designed and arranged such that forces, via which the second extension device can be pivoted about the second upper pivot axis, and forces, via which the second extension device can be pivoted about the second lower pivot axis, can be introduced into the second extension device via the second receptacle.

2. The device according to claim 1, characterized in that the first actuating device is designed to adjust the change in distance between the lower pivot axes or the pivot movement about the upper pivot axes by changing the length of a length-adjustable section of a first adjusting element, such that a section of a first threaded rod, and that the second actuating device is designed to perform the pivoting movement about the lower pivot axes by changing the length of a length-adjustable section of a second adjusting element.

3. The device according to claim 2, characterized in that the first adjusting element is mounted in a first guide assigned to the first extension device and in a second guide assigned to the second extension device and the length-adjustable section of the first adjusting element extends from the first guide to the second guide.

4. The device according to claim 2, characterized in that the second adjusting element is mounted in a further third guide assigned to the first extension device and in a further fourth guide assigned to the second extension device and the variable-length section of the second adjusting element extends from the further third guide to the further fourth guide.

5. The device according to claim 3, characterized in that the first guide is pivotable about the first receptacle and that the second guide is pivotable about the second receptacle.

6. The device according to claim 3, characterized in that each of the first and second guides are arranged at a distance from the corresponding receptacle in a plane orthogonal to the corresponding upper pivot axis and is connected to this via an inherently rigid connecting element which is pivotable with respect to the corresponding receptacle and the first and second guides are elongated and orthogonal to the corresponding upper pivot axis.

7. The device according to claim 3, characterized in that a receptacle-side arm is arranged non-rotatably opposite one of the receptacles and extends from the receptacle to a coupling element spaced from the receptacle and connected pivotably with the arm, which coupling element in turn is pivotably connected to a guide-side arm, which in turn extends from the pivotable connection with the coupling element to the guide and is arranged non-rotatably relative to this, wherein both first and second guides are connected to the respective receptacles in this way, wherein the non-rotatable connection between the receptacle and the receptacle-side arm and the non-rotatable connection between the guide and the guide-side arm is temporarily detachable, so that the angular position between the receptacle and the receptacle-side arm or between the first and second guides and the respective guide-side arm is freely pivotable.

8. The device according to claim 3, characterized in that the first and second guides are non-rotatably connected to a guide-side toothed section and the first and second receptacle, respectively, is non-rotatably connected to a receptacle-side toothed section which, via a gear arranged on the guide-side toothed section and the receptacle-side toothed section is in engagement with the guide-side toothed section and the receptacle-side toothed section, is coupled in terms of movement such that the guide-side toothed section and the receptacle-side toothed section have co-rotating directions of rotation wherein both first and second guides are connected to the respective receptacles in this way.

9. The device according to claim 8, characterized in that the guide with the guide-side toothed section extends via an inherently rigid connecting element that can be pivoted relative to the corresponding receptacle and relative to the guide, and is formed elongated and orthogonal to the corresponding upper pivot axis, is connected to the corresponding receptacle, the gear being rotatably mounted on the connecting element, wherein both guides are spaced and connected with the respective receptacles in this way.

10. The device according to claim 8, characterized in that the non-rotatable connection between the receptacle and the receptacle-side toothed section and/or between the guide and the guide-side toothed section is temporarily detachable, so that the angular position between the receptacle and the receptacle-side toothed section or between the guide and the guide-side toothed section is freely pivotable.

11. The device according to claim 1, characterized in that at least one receptacle is designed with a resiliently deflectable leg extending along a circumferential and longitudinal direction of the extension device, which leg can be placed from the outside on the outer circumference of the extension device, the leg having an outer wall and an inner wall, which are connected to one another at least one point in such a way that when pulling outer wall and inner wall against one another in the radial direction of the extension device, at a tension introduction point by means of a tension introduction mechanism, a compressive stress in the outer wall acting in the circumferential direction of the extension device starting from the tension introduction point, and a tensile stress in the inner wall acting in the opposite circumferential direction is generated, whereby the leg is forced against the outer circumference of the extension device and the receptacle can thereby be arranged in a clamping manner on the extension device.

12. A system comprising a device according to claim 1 and two extension devices which are received in the receptacles and two bone anchors each with a fork head, the device being designed such that the lower pivot axes are located in a region of the extension devices in which the extension devices contact the bone anchors when they are attached to the bone anchors, or that the lower pivot axes each extend through the bone anchors when the extension devices with the bone anchors attached are received in the device, wherein the lower pivot axes run through the fork head outside of the extension devices.

13. The system according to claim 12, wherein the extension devices at their lower end are spaced from the device and are not in contact with the device in this area.

* * * * *